US012370077B2

(12) United States Patent
Cohen et al.

(10) Patent No.: US 12,370,077 B2
(45) Date of Patent: Jul. 29, 2025

(54) FALLOPIAN TUBE RETRIEVABLE DEVICE

(71) Applicant: TEL HASHOMER MEDICAL RESEARCH INFRASTRUCTURE AND SERVICES LTD., Ramat Gan (IL)

(72) Inventors: Shlomi Cohen, Michmoret (IL); Tamir Ben David, Tel Aviv (IL); Tovy Sivan, Kfar Saba (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 195 days.

(21) Appl. No.: 17/927,987

(22) PCT Filed: May 27, 2021

(86) PCT No.: PCT/IL2021/050634
§ 371 (c)(1),
(2) Date: Nov. 28, 2022

(87) PCT Pub. No.: WO2021/245653
PCT Pub. Date: Dec. 9, 2021

(65) Prior Publication Data
US 2023/0310204 A1 Oct. 5, 2023

Related U.S. Application Data

(60) Provisional application No. 63/032,654, filed on May 31, 2020.

(51) Int. Cl.
*A61F 6/22* (2006.01)
(52) U.S. Cl.
CPC .................................. *A61F 6/225* (2013.01)

(58) Field of Classification Search
CPC .... A61F 6/225; A61F 6/22; A61F 6/18; A61F 6/14; A61F 6/20; A61F 6/144;
(Continued)

(56) References Cited

U.S. PATENT DOCUMENTS

2005/0081862 A1 4/2005 Callister
2005/0187561 A1 8/2005 Lee-Sepsick
(Continued)

FOREIGN PATENT DOCUMENTS

WO 0013624 A1 3/2000

OTHER PUBLICATIONS

International Preliminary Report on Patentability for corresponding application PCT/IL2021/050634 filed May 27, 2021; Report dated Sep. 29, 2022.
(Continued)

*Primary Examiner* — Ophelia A Hawthorne
(74) *Attorney, Agent, or Firm* — CANTOR COLBURN LLP

(57) ABSTRACT

A contraceptive device is provided including an occluding component for deployment in a tubal lumen of a reproductive organ. The device includes an expandable frame reversibly expandable from a collapsed state to an expanded state and a barrier supported by the expandable frame. In the expanded state the barrier is disposed between the expandable frame and walls of the lumen to inhibit in-growth of cellular material into and onto the occluding component, and additionally the barrier is urged against walls of the tubal lumen to define at least two tube lumen sealing areas, disposed perpendicular to a longitudinal axis of the walls of the tube lumen such that (i) the expandable frame is disposed between the two tubal lumen sealing surface, and (ii) passage of reproductive cells through the expandable frame, and through the tube lumen is blocked, therefore, creating a the
(Continued)

complete blockage for liquids from a first part of the tube to a second part of the tube, downstream the first part. Other applications are also described.

14 Claims, 10 Drawing Sheets

(58) Field of Classification Search
CPC .......... A61B 17/1204; A61B 17/12172; A61B 17/12177; A61K 9/0036; A61K 9/0039
See application file for complete search history.

(56) References Cited

U.S. PATENT DOCUMENTS

| 2012/0192872 | A1 | 8/2012 | Rudakov et al. |
| 2015/0007827 | A1* | 1/2015 | Ozdil ........................ A61F 6/22 128/831 |
| 2018/0369013 | A1 | 12/2018 | Brohm-Schmitz-Rode |
| 2019/0290475 | A1 | 9/2019 | Chin |

OTHER PUBLICATIONS

International Search report for corresponding application PCT/IL2021/050634 filed May 27, 2021; Report dated Aug. 23, 2021.
Written Opinion for corresponding application PCT/IL2021/050634 filed May 27, 2021; Report dated Aug. 23, 2021.

\* cited by examiner

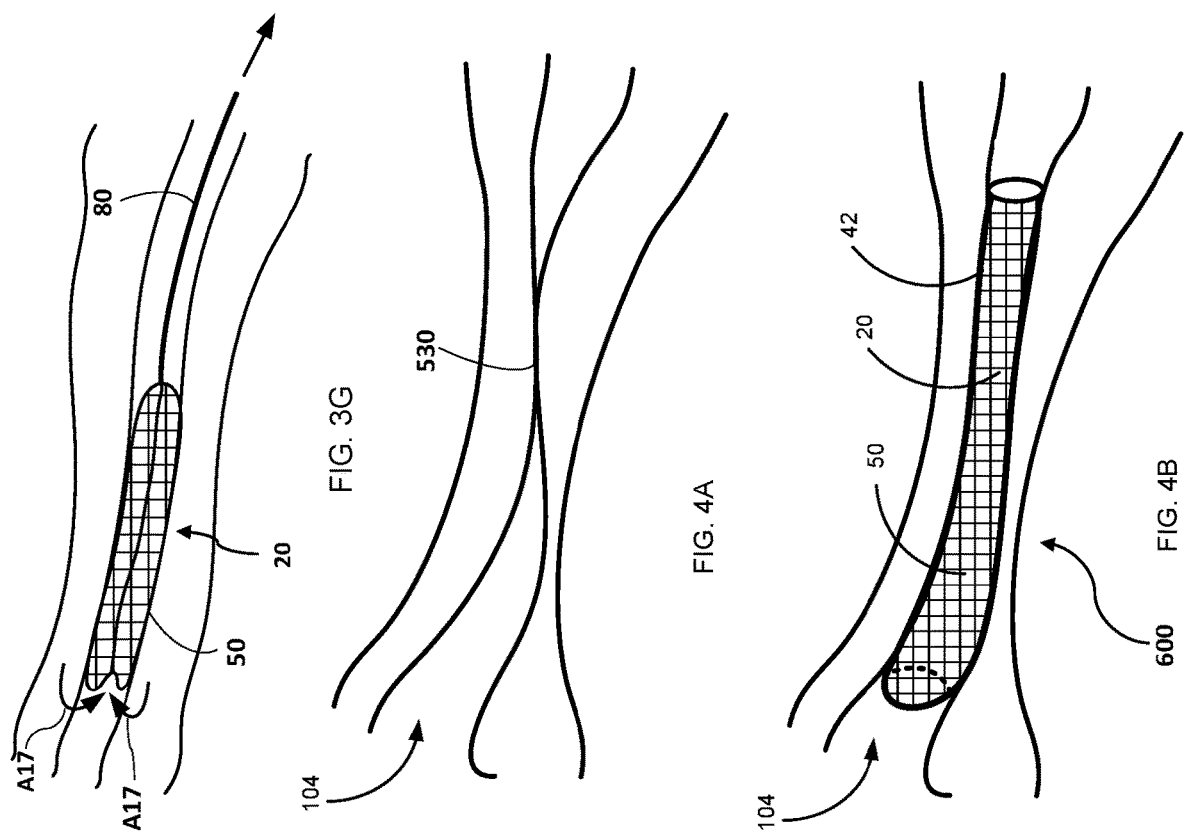

FALLOPIAN TUBE RETRIEVABLE DEVICE

FIELD OF THE INVENTION

Some applications of the present invention relate generally to medical devices and specifically to medical devices for deployment in a reproductive organ.

BACKGROUND

Contraception is the prevention of a pregnancy typically by either preventing fertilization of an egg cell by sperm or preventing attachment of a fertilized egg to the endometrial lining of the uterus.

Various contraception measures exist.

Barrier methods which include condoms, diaphragms and cervical caps are commonly used as birth control to prevent unattended pregnancies.

Additionally, hormonal options exist including oral contraceptives and injectable hormones or iud's containing hormones typically interfere with the normal hormonal cycle required for conception.

Intrauterine devices (IUD) and contraceptive implants are generally considered long-acting and reversible contraception.

Alternatively, male or female sterilization is a permanent approach for preventing a pregnancy. Sterilization procedures for women typically involve permanent occlusion or ligation of fallopian tubes, and sterilization procedures for males typically involve a vasectomy in which vas deferens tubes that carry sperm from the testes are sealed to prevent the release of sperm.

GENERAL DESCRIPTION

Contraceptive devices and methods for occlusion of a tube lumen in a reversible manner are provided, in accordance with some applications of the present invention.

The present disclosure provides a reversibly expandable device for contraception that is configured for introduction into the fallopian tube in a collapsed state and once in position, the device is configured to expand such that at least portions of it are pressed against the walls of the fallopian tube in a manner that entirely blocks the fallopian tube. The device has a frame that is enveloped by a sealing member or a barrier, e.g. a membrane or a sheet, such that when it is in its expanded form and pressed against the walls of the fallopian tube, passage of fluid within the fallopian tube and through the device is prevented. The sealing member is selected such that it prevents in-growth of biological tissues into the boundaries of the device, namely into an inner volume confined by the sealing member.

While the device of the present disclosure, as described in any of its aspects or embodiments, may be used for other purposes than contraception. Therefore, it should be understood that the device itself may be used for occluding or reversibly occluding other tubular organs of mammals, in particular humans.

It is to be noted that the term "frame" should be interpreted as any structure, skeleton, scaffold, or mesh that has the capability of expansion from a first state to a second state and also returning from the second state to the first state. Therefore, the term "frame" is interchangeable with the term "mesh", "skeleton", "complex", "scaffold" or "support".

The device, in its expanded form, may have several shapes, each of them has one or more contact profiles with the lumen of the fallopian tube. For example, the device may have a shape of a hourglass or a nut with two circumferential portions that are pressed against the walls of the fallopian tube allowing the anchoring of the device in position within the tube, thereby occluding passage of sperm or egg cells therethrough.

In some configurations of the device, it is equipped with a guiding thread to facilitate removal thereof from the fallopian tube, should such a need arise. In one alternative, removal of the device includes a coupling arrangement at a proximal end of the device for coupling with a removal tool.

The frame of the device may be collapsible to allow to retrieve the reproductive functionality of the fallopian tube, namely to allow flow of reproductive material through the fallopian tube and the device. In some configuration this is achieved by including portions in the frame that are breakable or puncturable such that upon application of force thereon the device collapses to an extent passage of fluid through the fallopian tube is retrieved.

For some applications, the contraceptive device comprises one or more barriers supported by an expandable frame. Typically, the barrier comprises an impermeable membrane that inhibits passage of cellular material therethrough. For some applications, the impermeable barrier membrane fully encapsulates the frame. The expandable frame is reversibly expandable from a collapsed state to an expanded state such that the barrier assumes an expanded state when the expandable frame is in the expanded state.

The contraceptive device is typically deployed in the tube lumen such that when expanded in the lumen, the surface, or at least edges of the impermeable barrier are urged against a wall of the tube lumen resulting in occlusion and a complete seal of the tube lumen.

The term "tube lumen" throughout the application is interchangeable with the term "tubal lumen".

For some applications, the contraceptive device is typically deployed in a tube lumen of a reproductive organ, e.g., a Fallopian tube. When deployed in the tube lumen and expanded to the expanded state, the impermeable barrier disposed between the expandable frame and the wall of the lumen inhibits in-growth of cellular material into and onto the occluding contraceptive device that may render the device non-retrievable.

When expanded inside the tube lumen the impermeable barrier inhibits passage through the tube lumen by mechanically blocking the tube lumen. For some applications, when expanded in the tubal lumen, the impermeable barrier defines at least two tubal lumen sealing surfaces. It is to be noted that the term "sealing surfaces" refers to a continuous circumferential interface of the impermeable barrier and the internal walls of the tubal lumen that blocks passage of reproductive cells from one side of the interface to another side thereof downstream the natural flow path of the reproductive cells. In other words, the sealing surface causes an interruption of bilateral movement within the tube. Therefore, the term "sealing surfaces" may be interchangeable with the term "sealing area", "sealing profile" or "circumferential sealing". Each one of the at least two tubal lumen sealing surfaces are urged against the lumen wall and are disposed at an angle (e.g., generally perpendicular) with respect to the longitudinal axis of the tube, thereby forming a double barrier by inhibiting passage both proximally and distally in the tube lumen.

In some applications, each of the at least two tube lumen sealing surfaces is disposed at opposite end portions of the contraceptive device e.g., one surface at a proximal end portion and a second surface at a distal end portion or mid portion. Typically, a first one of the at least two tube lumen sealing surfaces is supported by a proximal end portion of the expandable frame such that passage through the proximal end of the expandable frame is blocked by the first tube sealing surface. Additionally, a second one of the at least two sealing surfaces is supported by a distal end portion of the expandable frame such that passage through the distal end of the expandable frame is blocked by the second tube sealing surface. Consequently, passage through the expandable frame and through the tube lumen is blocked when the expandable frame is expanded in the tube lumen such that the sealing surfaces are urged against the wall of the tube lumen. In some applications, in the expanded state, the frame supports the at least two tube lumen sealing surfaces and is disposed therebetween.

As described hereinabove, the contraceptive device is configured to provide a reversible contraceptive. For some such applications, the contraceptive device further comprises a retrieval element for facilitating retrieval of the contraceptive device from the tube lumen. For example, the contraceptive device comprises a cord or a thread coupled to the impermeable barrier (or the expandable frame) such that pulling of the cord in a proximal direction causes dislodging of the contraceptive device and facilitates sliding of the contraceptive device out of the tube lumen (it is noted that an additional removal tool, e.g., a crimping over-tube, may be used to facilitate retrieval of the contraceptive device as will be described elsewhere herein). Alternatively, or additionally, reversibility of the contraceptive device may be facilitated by mechanical disruption of the barrier to allow passage of reproductive cells through the expandable frame and the tube lumen.

For some applications, the contraceptive device is shaped and sized for occlusion of a Fallopian tube of a female subject for providing long-term, yet reversible occlusion of the Fallopian tube, thereby attaining a reliable, long-term and reversible contraception measure.

Typically, for such applications, the contraceptive device is transcervically advanced towards the Fallopian tube and deployed in the Fallopian tube lumen. Upon deployment, the expandable frame self-expands such that the impermeable barrier is expanded from a collapsed state into an expanded state in the Fallopian tube lumen. In the expanded state, the lumen of the Fallopian tube is fully occluded to prevent passage both proximally and distally through the expandable frame and through the tube lumen. As a result, fertilization of the egg by the sperm is inhibited thereby preventing a pregnancy.

When desired, the contraceptive device is retrieved from the Fallopian tube lumen. For some applications the retrieval element is used to facilitate removal of the contraceptive device from the lumen of the Fallopian tube, to restore fertility and allow for fertilization between the egg and sperm to occur. Additionally, or alternatively, the impermeable barrier is disrupted to allow passage of reproductive cells through the frame and tube lumen thereby removing the seal without retrieving the contraceptive device from the Fallopian tube. For example, the barrier may be mechanically disrupted to create an aperture by tearing or puncturing the barrier by a physician when restoring fertility is desired.

There is therefore provided in accordance with some applications of the present invention, a contraceptive device including:

an occluding component shaped and sized to be deployed in a tube lumen of a reproductive organ and including:
an expandable frame reversibly expandable from a collapsed state to an expanded state;

a barrier supported by the expandable frame, such that when the frame is in the expanded state:
a) the barrier is disposed between the expandable frame and walls of the lumen. The barrier may inhibit in-growth of cellular material into and onto the occluding component;
b) the barrier is urged against walls of the tube lumen to define at least one, optionally two, lumen sealing surfaces, each disposed substantially perpendicular with respect to a longitudinal axis of the walls of the tube lumen such that (i) the expandable frame is disposed between the two tube lumen sealing surface, and (ii) passage of reproductive cells through the expandable frame, and through the tube lumen, is blocked when the expandable frame is expanded in the tube. It is to be noted that sealing surface is a consecutive and closed pattern of interface between the barrier and the lumen walls thus defining a sealing circumference of a portion of the lumen resulting in a blockage of passage of reproductive cells through the device.

For some applications, the device includes a retrieval element coupled to the occluding component.

For some applications, the frame is fully encapsulated by the barrier.

For some applications, the barrier includes an impermeable membrane.

For some applications, the barrier has an inner surface and an outer surface, and the inner surface of the barrier is disposed on an outer surface of the expandable frame.

For some applications, the barrier includes an elastic biocompatible material.

For some applications, the barrier includes at least one of the following materials: EPTFE, silicone, polyurethane, or any combination thereof.

For some applications, the barrier includes a non-adhesive material.

For some applications, the expandable frame includes an expandable shape-memory metal.

For some applications, the expandable frame includes an expandable mesh.

For some applications, the barrier is further configured to be mechanically breached to allow passage of reproductive cells through the expandable frame, and through the tube lumen, when the expandable frame is expanded in the tube.

For some applications, the expandable frame is shaped to define a proximal end portion at a proximal portion of the expandable frame and a distal end portion at a distal portion of the expandable frame, and a first one of the at least two tube lumen sealing surfaces is supported by the proximal end portion such that passage through the proximal end portion of the expandable frame is blocked by the first sealing surface, and a second one of the two sealing surfaces is supported by the distal end portion such that passage through the distal end portion of the expandable frame is blocked by the second sealing surface.

For some applications, a distance between the at least two sealing surfaces is 2-10 mm, in the expanded state.

For some applications, the distance between the at least two sealing surfaces is 4-6 mm, in the expanded state.

For some applications, the expandable frame includes at least one circumferential portion having a rigidity that is greater than a rigidity of remaining portions of the expandable frame.

For some applications, the at least one circumferential portion includes at least two circumferential portions, configured to contact the walls of the tube lumen to anchor the occluding component in the tube when the frame is in the expanded state.

For some applications, the at least one circumferential portion has a diameter of 2-15 mm.

For some applications, the expandable frame has a proximal portion, a distal portion and a middle portion disposed between the proximal and distal portions and when the frame is in the expanded state a cross section of each one of the proximal and distal portions is greater than a cross section of the middle portion such that a gap is formed between the middle portion and walls of the tube when the expandable frame is expanded in the tube lumen.

For some applications, the occluding component is shaped to define a peanut-like shape.

For some applications, a cross section area of the proximal portion is 10-400% times greater than a cross section area of the middle portion.

For some applications, a cross section area of the distal portion is 10-400% times greater than a cross section area of the middle portion.

For some applications, the device further includes a deployment tool and the device is shaped and sized to be advanced towards the tube lumen by the deployment tool in the collapsed state, and to self-expand into the expanded state upon deployment in the lumen of the tube by the deployment tool.

For some applications, a removal tool configured to remove the contraceptive device from the tube lumen.

For some applications, the removal tool includes an over-tube shaped and sized to be advanced distally over the contraceptive device to cause crimping of the contraceptive device into the over-tube to facilitate removal of the contraceptive device from the Fallopian tube.

For some applications, the tube lumen includes a lumen of a Fallopian tube, and the barrier is urged against the inner walls of the Fallopian tube in the expanded state.

For some applications, the occluding component is shaped and sized to be disposed entirely within the lumen of the tube and not to penetrate tissue of the tube.

For some applications, the expandable frame has a length of 10-80 mm in the expanded state, measured along a longitudinal axis of the expandable frame.

There is additionally provided in accordance with some applications of the present invention, a contraceptive device including:
an occluding component shaped and sized to be deployed in a tube lumen of a reproductive organ and including:
an expandable frame having a proximal portion, a distal portion and a middle portion disposed between proximal and distal portions, and reversibly expandable from a collapsed state to an expanded state; and
a barrier supported by the expandable frame, such that when the frame is in the expanded state:
  (a) the barrier is urged against walls of the tube lumen to define at least two tube lumen sealing surfaces, each disposed substantially perpendicular with respect to a longitudinal axis of the walls of the tube lumen such that (i) the expandable frame is disposed between the two tube lumen sealing surface, and (ii) passage of reproductive cells through the expandable element, and through the tube lumen, is blocked; and
  (b) a cross section of each one of the proximal and distal portions is greater than a cross section of the middle portion such that a gap is formed between the middle portion and walls of the tube when the expandable frame is expanded in the tube lumen.

For some applications, the device further includes a retrieval element coupled to the occluding component.

For some applications, a cross section area of the proximal portion is 10-400% times greater than a cross section area of the middle portion.

For some applications, a cross section area of the distal portion is 10-400% times greater than a cross section area of the middle portion.

For some applications, the occluding component is shaped to define a peanut-like shape.

For some applications, the barrier is further configured to be mechanically breached to allow passage of reproductive cells through the expandable frame, and through the tube lumen, when the expandable frame is expanded in the tube.

For some applications, the expandable frame is shaped to define a proximal end at the proximal portion and a distal end at the distal portion, and
a first one of the at least two tube lumen sealing surfaces is supported by the proximal end portion such that passage through the proximal end portion of the expandable frame is blocked by the first sealing surface, and a second one of the two sealing surfaces is supported by the distal end portion such that passage through the distal end portion of the expandable frame is blocked by the second sealing surface.

For some applications, a distance between the at least two sealing surfaces is 2-10 mm, in the expanded state.

For some applications, the distance between the at least two sealing surfaces is 4-6 mm, in the expanded state.

For some applications, the barrier is disposed between the frame and the walls of the tube lumen and thus typically inhibits in-growth of cellular material into and onto the occluding component.

For some applications, the barrier has an inner surface and an outer surface, and the inner surface of the barrier is disposed on an outer surface of the expandable frame.

For some applications, the expandable frame is entirely encapsulated by the barrier.

For some applications, the barrier includes an impermeable membrane.

For some applications, the barrier includes an elastic biocompatible material.

For some applications, the barrier includes at least one of the following materials: EPTFE, silicone. Polyurethane or any combination thereof.

For some applications, the barrier includes a non-adhesive material.

For some applications, the expandable frame includes an expandable shape-memory metal.

For some applications, the expandable frame includes an expandable mesh.

For some applications, the expandable frame has a length of 10-80 mm in the expanded state, measured along a longitudinal axis of the expandable frame.

For some applications, the expandable frame includes at least one circumferential portion having a rigidity that is greater than a rigidity of remaining portions of the expandable frame.

For some applications, the at least one circumferential portion includes at least two circumferential portions, configured to contact the walls of the tube lumen to anchor the occluding component in the tube when the frame is in the expanded state.

For some applications, the at least one circumferential portion has a diameter of 2-15 mm.

For some applications, the occluding component is shaped and sized to be disposed entirely within the lumen of the tube and not to penetrate tissue of the tube.

For some applications, the device further includes a deployment tool and the device is shaped and sized to be advanced towards the tube lumen by the deployment tool in the collapsed state, and to self-expand into the expanded state upon deployment in the lumen of the tube by the deployment tool.

For some applications, the device further includes a removal tool configured to remove the contraceptive device from the tube lumen.

For some applications, the removal tool includes an over-tube shaped and sized to be advanced distally over the contraceptive device to cause crimping of the contraceptive device into the over-tube to facilitate removal of the contraceptive device from the Fallopian tube.

For some applications, the tube lumen includes a lumen of a Fallopian tube and the barrier is urged against an inner wall of the Fallopian tube in the expanded state.

For some applications, the barrier includes a sealed bladder having a wall supported by the expandable frame such that when the expandable frame is in the expanded state the sealed bladder is expanded into a balloon-like state.

There is further provided in accordance with some applications of the present invention, a contraceptive device including:
an occluding component shaped and sized to be deployed in a tube lumen of a reproductive organ and including:
an expandable frame reversibly expandable from a collapsed state to an expanded state, and shaped to define at least one circumferential portion having a rigidity that is greater than a rigidity of remaining portions of the expandable frame;
a barrier supported by the expandable frame, such that when the frame is in the expanded state:
(a) the barrier is urged against walls of the tube lumen to define at least two tube lumen sealing surfaces, each disposed substantially perpendicular with respect to a longitudinal axis of the walls of the tube lumen such that (i) the expandable frame is disposed between the two tube lumen sealing surface, and (ii) passage of reproductive cells through the expandable element, and through the tube lumen, is blocked when the expandable frame is expanded in the tube lumen;
(b) the at least one circumferential portion contacts the walls of the tube lumen to anchor the occluding component in the tube.

For some applications, the device further includes a retrieval element coupled to the occluding component.

For some applications, the at least one circumferential portion includes at least two circumferential portions.

For some applications, the at least one circumferential portion has a diameter of 2-15 mm.

For some applications, the barrier is disposed between the frame and the walls of the tube lumen to inhibit in-growth of cellular material into and onto the occluding component.

For some applications, the barrier has an inner surface and an outer surface and the inner surface of the barrier is disposed on an outer surface of the expandable frame.

For some applications, the frame is fully encapsulated by the barrier.

For some applications, the barrier includes an impermeable membrane.

For some applications, the barrier includes an elastic biocompatible material.

For some applications, the barrier includes at least one of the following materials: EPTFE, silicone. Polyurethane or any combination thereof.

For some applications, the barrier includes a non-adhesive material.

For some applications, the expandable frame includes an expandable shape-memory metal.

For some applications, the expandable frame includes an expandable mesh.

For some applications, the barrier is further configured to be mechanically breached to allow passage of reproductive cells through the expandable frame, and through the tube lumen, when the expandable frame is expanded in the tube.

For some applications, the expandable frame is shaped to define a proximal end portion at a proximal portion of the expandable frame and a distal end portion at a distal portion of the expandable frame, and
a first one of the at least two tube lumen sealing surfaces is supported by the proximal end portion such that passage through the proximal end portion of the expandable frame is blocked by the first sealing surface, and a second one of the two sealing surfaces is supported by the distal end portion such that passage through the distal end portion of the expandable frame is blocked by the second sealing surface.

For some applications, a distance between the at least two sealing surfaces is 2-10 mm, in the expanded state.

For some applications, the distance between the at least two sealing surfaces is 4-6 mm, in the expanded state.

For some applications, the expandable frame has a proximal portion, a distal portion and a middle portion disposed between the proximal and distal portions and when the frame is in the expanded state a cross section of each one of the proximal and distal portions is greater than a cross section of the middle portion such that a gap is formed between the middle portion and walls of the tube when the expandable frame is expanded in the tube lumen.

For some applications, the occluding component is shaped to define a peanut-like shape.

For some applications, a cross section area of the proximal portion is 10-400% times greater than a cross section area of the middle portion.

For some applications, a cross section area of the distal portion is 10-400% times greater than a cross section area of the middle portion.

For some applications, the device further includes a deployment tool and the device is shaped and sized to be advanced towards the tube lumen by the deployment tool in the collapsed state, and to self-expand into the expanded state upon deployment in the lumen of the tube by the deployment tool.

For some applications, the device further includes a removal tool configured to remove the contraceptive device from the tube lumen.

For some applications, the removal tool includes an over-tube shaped and sized to be advanced distally over the contraceptive device to cause crimping of the contraceptive device into the over-tube to facilitate removal of the contraceptive device from the Fallopian tube.

For some applications, the tube lumen includes a lumen of a Fallopian tube and the barrier is urged against the inner walls of the Fallopian tube in the expanded state.

For some applications, the occluding component is shaped and sized to be disposed entirely within the lumen of the tube and not to penetrate tissue of the tube.

For some applications, the expandable frame has a length of 10-80 mm in the expanded state, measured along a longitudinal axis of the expandable frame.

There is further provided in accordance with some applications of the present invention, a method for reversibly occluding a lumen of a Fallopian tube of a subject, the method including:
  transcervically advancing towards the lumen of the Fallopian tube, a device in a collapsed state including an impermeable barrier supported by an expandable frame reversibly expandable from a collapsed state to an expanded state,
  deploying the device in the lumen of the Fallopian tube, causing the expandable frame to self-expand such that the impermeable barrier is urged against a wall of the lumen to define at least two tube lumen sealing surfaces (a) that are disposed substantially perpendicular with respect to the wall of the tube lumen, and (b) disposed such that the expandable frame is disposed between the two tube lumen sealing surface;
  blocking passage of reproductive cells (i) through expandable frame, and (ii) through the lumen of the Fallopian tube by deploying the device in the lumen; and
  subsequently to the blocking, restoring passage of reproductive cells through the tube lumen by disrupting the at least two sealing surfaces.

For some applications, disrupting the sealing surface includes creating an aperture in the sealing surface.

For some applications, disrupting the sealing surface includes removing the sealing surface.

For some applications, the method further includes blocking passage of reproductive cells (i) through expandable frame, and (ii) through the lumen of the Fallopian tube by deploying an occluding element within the expanded frame, subsequently to disrupting the at least two sealing surfaces.

For some applications, deploying an occluding element within the expanded frame, subsequently to disrupting the at least two sealing surfaces, includes inflating an occluding balloon within the expanded frame.

For some applications, deploying includes deploying the device in an uterotubal junction of the Fallopian tube.

For some applications, deploying the device in the lumen of the Fallopian tube includes inhibiting cell in-growth into and onto the device by deploying the device such that the impermeable barrier is disposed between the expandable frame and walls of the Fallopian tube.

For some applications, the expandable frame includes at least one circumferential portion having a rigidity that is greater than a rigidity of remaining portions of the expandable frame, and the method further includes anchoring the frame by contacting the at least one circumferential portion against the wall of the Fallopian tube.

For some applications, the expandable frame has a proximal portion, a distal portion and a middle portion disposed between the proximal and distal portions, and deploying the device includes deploying the device such that a gap is formed between the middle portion and the wall of the Fallopian tube.

For some applications, the method further includes assessing a cross section of the Fallopian tube and selecting a size and a shape of the device for deployment based on the assessed cross section.

For some applications, the method further includes assessing a diameter of the Fallopian tube and selecting a size and a shape of the device for deployment based on the assessed diameter.

For some applications, the device further includes a retrieval element and the method further includes retrieving the device from the lumen of the Fallopian tube using the retrieval element.

For some applications, the device further includes a removal tool and removing the device further includes removing the device from the lumen of the Fallopian tube using the removal tool.

For some applications, removing the device using the removal tool includes:
  advancing the removal tool distally over the contraceptive device;
  using the retrieval element, inhibiting distal movement of the contraceptive device during the advancing the removal tool distally over the contraceptive device;
  causing crimping by radial compression of the expandable frame into the removal tube such that the contraceptive device is disposed in the removal tool; and
  removing the device out of the lumen of the Fallopian tube by retracting the removal tool proximally.

There is further provided in accordance with some applications of the present invention, a method for reversibly occluding a lumen of a Fallopian tube of a subject, the method including:
  transcervically advancing towards the lumen of the Fallopian tube, a device in a collapsed state including:
    (i) an occluding component including an impermeable barrier supported by an expandable frame reversibly expandable from a collapsed state to an expanded state, and
    (ii) a retrieval element coupled to the occluding component;
  deploying the device in the lumen of the Fallopian tube, causing the expandable frame to self-expand such that the impermeable barrier is urged against a wall of the lumen to define at least two tube lumen sealing surfaces (a) that are disposed substantially perpendicular with respect to the wall of the tube lumen, and (b) disposed such that the expandable frame is disposed between the two tube lumen sealing surface;
  blocking passage of reproductive cells (i) through expandable frame, and (ii) through the lumen of the Fallopian tube by deploying the device in the lumen; and
  using the retrieval element, retrieving the device from the lumen of the Fallopian tube.

For some applications, deploying includes deploying the device in an uterotubal junction of the Fallopian tube.

For some applications, removing the device from the lumen of the Fallopian tube using the retrieval element includes pulling the retrieval element in a proximal direction.

For some applications, removing the device, includes causing (i) narrowing of the expandable frame by pulling the retrieval element in a proximal direction; and (ii) sliding the device out of the lumen of the Fallopian tube.

For some applications the method includes:
  advancing the removal tool distally over the contraceptive device;
  using the retrieval element, inhibiting distal movement of the contraceptive device during the advancing the removal tool distally over the contraceptive device;
  causing crimping by radial compression of the expandable frame into the removal tube such that the contraceptive device is disposed in the removal tool; and
  removing the device out of the lumen of the Fallopian tube by retracting the removal tool proximally.

For some applications, deploying the device in the lumen of the Fallopian tube includes inhibiting cell in-growth into and onto the occluding component by deploying the occluding component such that the impermeable barrier is disposed between the expandable frame and walls of the Fallopian tube.

For some applications, the expandable frame includes at least one circumferential portion having a rigidity that is greater than a rigidity of remaining portions of the expandable frame, and the method further includes anchoring the occluding component by contacting the at least one circumferential portion against the wall of the Fallopian tube.

For some applications, the expandable frame has a proximal portion, a distal portion and a middle portion disposed between the proximal and distal portions, and deploying the occluding component includes deploying the occluding component such that a gap is formed between the middle portion and the wall of the Fallopian tube.

For some applications, the method further includes assessing a cross section of the Fallopian tube and selecting a size and a shape of the occluding component for deployment based on the assessed cross section.

For some applications, the method further includes assessing a diameter of the Fallopian tube and selecting a size and a shape of the occluding component for deployment based on the assessed diameter.

There is further provided in accordance with some applications of the present invention, a method for treating infertility in women, the method including:
  transcervically advancing towards the lumen of the Fallopian tube, a device in a collapsed state including a barrier supported by an expandable frame reversibly expandable from a collapsed state to an expanded state;
  deploying the device in the lumen of the Fallopian tube, causing the expandable frame to self-expand urging the barrier against a wall of the lumen such that the barrier is disposed between the expanded frame and the wall of the Fallopian tube along a longitudinal axis of the frame and the Fallopian tube; and
  maintaining the Fallopian tube in an open state by deploying the device in the lumen of the Fallopian tube.

For some applications, maintaining the Fallopian tube in an open state includes allowing passage of reproductive cells through the expandable frame, and through the tube lumen.

For some applications, deploying the device includes deploying the device such that the barrier is disposed between the expandable frame and walls of the tube lumen to inhibit in-growth of cellular material into and onto the device.

For some applications, deploying the device includes deploying the device such that the barrier does not occlude passage of reproductive cells through proximal and distal portions of the device.

There is further provided in accordance with some applications of the present invention, a device shaped and sized to be deployed in a tube lumen of a reproductive organ, the device including:
  an expandable frame reversibly expandable from a collapsed state to an expanded state; and
  a barrier supported by the expandable frame, when the frame is deployed in the expanded state in the tube lumen:
    (a) the barrier is disposed between the expandable frame and walls of the tube lumen to inhibit in-growth of cellular material into and onto the device;
    (b) the tube lumen is maintained in an open state allowing passage of reproductive cells through the expandable frame, and through the tube lumen.

There is further provided in accordance with some applications of the present invention, a kit including:
  a contraceptive device including:
    (i) an occluding component including an impermeable barrier supported by an expandable frame reversibly expandable from a collapsed state to an expanded state, and
    (ii) a retrieval element coupled to the occluding component;
  a deployment tool configured to advance the contraceptive device into a tube lumen; and
  a removal tool configured to remove the contraceptive device from the tube lumen.

The present invention will be more fully understood from the following detailed description of embodiments thereof, taken together with the drawings, in which:

BRIEF DESCRIPTION OF THE DRAWINGS

FIG. 3G is a schematic illustration of the contraceptive device being retrieved from the lumen of the Fallopian tube using a retrieval element, in accordance with some applications of the present invention;

FIG. 4A is a schematic illustration of a naturally occurring occlusion in a Fallopian tube causing infertility in a female; and FIG. 4B is a schematic illustration of a device for treating infertility due to naturally occurring occlusion in a Fallopian tube causing infertility in a female, in accordance with some applications of the present invention.

DETAILED DESCRIPTION

Figure 1:
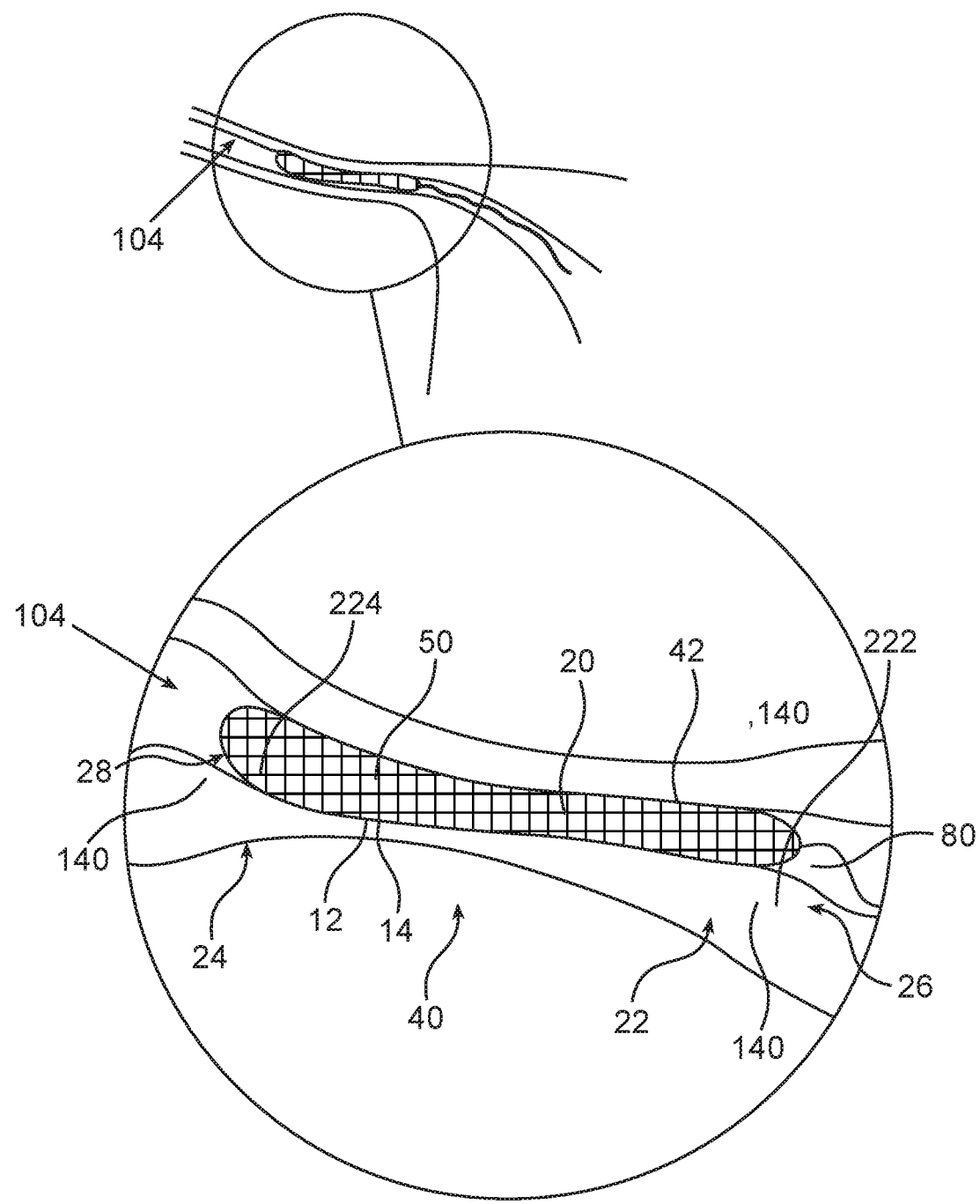
FIG. 1 is a schematic illustration of a contraceptive device deployed in the lumen of the Fallopian tube in an expanded state, in accordance with some applications of the present invention.

Some aspects of the present invention provide a contraceptive device for occluding a tube lumen in a body of a subject in a reversible manner. Typically, the contraceptive device comprises an occluding component and a retrieval component.

In some aspects, the contraceptive device comprises an occluding component comprising an impermeable barrier supported by an expandable frame reversibly expandable from a collapsed state to an expanded state. The contraceptive device is typically advanced toward the lumen of the tube in the collapsed state and once deployed in the lumen of the tube, is self-expanded into an expanded state in the tube lumen such that the impermeable barrier is disposed against an inner wall of the tube lumen to completely occlude the lumen of the tube. Typically, the contraceptive device additionally comprises a retrieval element for facilitating removal of the occluding component from the tube lumen, rendering the occlusion reversible.

In some aspects, the impermeable barrier defines at least two lumen sealing surfaces urged against the tube lumen wall and disposed at an angle (e.g., generally perpendicular) with respect to the longitudinal axis of the tube, thereby forming a double barrier by inhibiting passage both proximally and distally in the tube lumen.

In some aspects the expandable frame is disposed between the at least two lumen sealing surfaces.

In some aspects, a first one of the at least two tube lumen sealing surfaces is supported by a proximal end portion of the expandable frame such that passage through the proximal end portion of the expandable frame is blocked by the first lumen sealing surface. Additionally, a second one of the at least two lumen sealing surfaces is supported by a distal end portion of the expandable frame such that passage through the distal end portion of the expandable frame is blocked by the second lumen sealing surface. Thus, inhibiting passage both proximally and distally through the expandable frame and through the tube lumen.

In some aspects, the impermeable barrier comprises a sealed bladder having a wall supported by the expandable frame reversibly expandable from a collapsed state to an expanded state. The contraceptive device is typically advanced toward the lumen of the tube in the collapsed state and once deployed in the lumen of the tube, is self-expanded into an expanded state in the tube lumen such that the wall of the bladder is disposed against an inner wall of the tube lumen to completely occlude the lumen of the tube.

In some aspects of the invention, the contraceptive device is shaped and sized for occluding a reproductive lumen of a female subject, e.g., for occluding a Fallopian tube.

In some aspects, in the expanded state, the impermeable barrier is urged against the Fallopian tube wall and generally assumes the shape of the wall to uniformly distribute the pressure applied by the impermeable barrier along the Fallopian tube wall, form a seal between the barrier and the wall along the surface of the expandable frame and prevent wrinkles and convolutions in the fallopian tube wall that may form undesired passageways for reproductive cells.

In some aspects, the expandable frame has a proximal portion, a distal portion and a middle portion disposed between proximal and distal portions, and a cross section area of each one of the proximal and distal portions is greater than a cross section area of the middle portion thereby resembling a peanut or an hourglass shape. Consequently, in some aspects, when the expandable frame is expanded in the tube lumen, a gap is formed between the middle portion and walls of the tube, such that the wall of the tube lumen is contacted only by at least a portion of the distal and proximal portions of the expandable frame.

In some aspects, the expandable frame is shaped to define at least one circumferential portion, e.g., two portions, having a rigidity that is greater than a rigidity of remaining portions of the expandable frame. Typically, the expandable frame is anchored to the wall of the tube lumen by anchoring the portions of greater rigidity against the walls of the lumen. In some applications, the higher rigidity portions comprise one or more circumferential rings made of axially compressed frame material (e.g., mesh). In some applications, the higher rigidity portions comprise one or more circumferential rings made of an expandable material higher in rigidity than the remaining portions of the device frame.

In some aspects, the contraceptive device is configured to provide a reversible and retrievable contraceptive device.

In some aspects, the impermeable barrier is disposed between the expandable frame and walls of the lumen to inhibit in-growth of cellular material into and onto the occluding component, (e.g., in-growth which may render the contraceptive device irretrievable). In particular, in some aspects the impermeable barrier comprises an elastic biocompatible material (e.g., EPTFE, silicone or polyurithane) and/or a non-adhesive material which prevent the in-growth of cellular material into and onto the occluding component. Consequently, the contraceptive device can be easily and safely retrieved from the Fallopian tube when desired without harming tissue of the tube.

In some aspects, the occluding component is completely disposed in the Fallopian tube lumen and does not comprise barbs and/or hooks that penetrate tissue of the Fallopian tube. Consequently, the contraceptive device can be easily and safely retrieved from the Fallopian tube when desired without harming tissue of the tube.

The contraceptive device typically comprises a retrieval element for facilitating retrieval of the contraceptive device from the tube lumen. For example, the contraceptive device comprises a cord, a thread, and/or a wire loop coupled to the impermeable barrier (or the expandable frame) such that pulling of the retrieval element in a proximal direction facilitates sliding of the contraceptive device out of the tube lumen. Additionally, or alternatively, a removal tool, e.g., an over-tube, may be used to facilitate retrieval of the contraceptive device. Optionally, the over-tube is configured to be advanced distally over the contraceptive device while causing crimping of the expandable frame, and thereby facilitating removal of the contraceptive device from the tube lumen.

In some aspects, apparatus and method for reversing the occlusion and restoring fertility while the contraceptive device is deployed in the lumen of the Fallopian tube are provided. Typically, the barrier which is supported by the expandable frame is disrupted, e.g., punctured or torn in a controlled manner by a physician, thereby allowing passage of reproductive cells through the frame and through the lumen of the Fallopian tube to restore fertility. In some aspects, when it is desirable to re-occlude the Fallopian tube, an occluding element such as a balloon is inflated in the expandable frame to re-block the Fallopian tube.

Reference is now first made to FIG. 1 which is a schematic illustration of contraceptive device 20 deployed in the lumen of a Fallopian tube 104 in an expanded state, in accordance with some applications of the present invention.

Contraceptive device 20 typically comprises an occluding component comprising a barrier 140, e.g., an impermeable barrier 140, supported by an expandable frame 50. Expandable frame 50 is reversibly expandable from a collapsed state to an expanded state such that barrier 140 assumes an expanded state when expandable frame 50 is in the expanded state.

Impermeable barrier 140 typically comprises a non-permeable barrier such that passage through barrier 140 is blocked. For example, barrier 140 comprises a non-permeable elastic biocompatible material and/or coating (e.g., e.g., polyurethane, silicone, EPTFE, and/or Dacron). Impermeable barrier 140 is shaped to define an inner surface 12 and an outer surface 14, and is typically disposed such that inner surface 12 is placed in contact with frame 50 and outer surface 14 is placed in contact with the lumen wall when contraceptive device 20 deployed in the lumen of a Fallopian tube 104 in the expanded state. As shown, impermeable barrier 140 is typically disposed to encapsulate frame 50 and prevent in-growth of cellular material into and onto contraceptive device 20 for ensuring the reversibility of contraceptive device 20 and facilitating retrieval of the contraceptive device in simple and safe manner.

Additionally, or alternatively, barrier 140 comprises a non-adhesive material inhibiting tissue in-growth in and on barrier 140, for ensuring the reversibility of contraceptive device 20 functionality by facilitating retrieval of the contraceptive device in simple and safe manner.

FIG. 1 shows contraceptive device 20 in the expanded state such that contraceptive device 20 fills the lumen of tube 104 and contacts the walls of the lumen, to occlude the lumen. Optionally but not necessarily, contraceptive device 20 is shaped and sized to expand within the lumen of tube 104 to conform to the natural shape of tube 104, such that contraceptive device 20 fits snugly within tube 104. Alternatively, at least 40%-100%, e.g., at least 50%-75%, 40%-60%, 60%-80%, or 80%-100%, of contraceptive device 20 contacts the walls of the lumen. For example, the wall of the tube lumen is contacted only by at least a portion of the distal and proximal portions of the expandable frame.

When expanded in the lumen of tube 104, impermeable barrier 140 forms a double barrier by defining at least two tube lumen sealing surfaces, e.g., first and second tube lumen sealing surfaces 26 and 28. First and second sealing surfaces 26 are each disposed at an angle (e.g., generally perpendicular) with respect to the longitudinal axis of tube 104 and contact walls of lumen of tube 104 to form a double barrier by inhibiting passage proximally through first sealing surface 26 and distally through second surface 28.

Typically, first sealing surface 26 is supported by a proximal end portion 222 at a proximal portion 22 of expandable frame 50. First sealing surface 26 of barrier 140 is disposed such that passage through proximal end 222 of expandable frame 50 is blocked. Additionally, second sealing surface 28 is supported by a distal end portion 224 at a distal portion 24 of expandable frame 50. Second sealing surface 28 of barrier 140 is disposed such that passage through distal end 224 of expandable frame 50 is blocked. Consequently, passage through expandable frame 50 and through the lumen of tube 104 is blocked when expandable frame 50 is expanded in the lumen of tube 104 such that (i) sealing surfaces 26 and 28 are disposed in contact and at an angle with respect to the wall of tube 104, and (ii) expandable frame 50 is disposed between sealing surfaces 26 and 28.

For some applications, in the expanded state, a distance between the sealing surfaces 26 and 28 is 2-10 mm, e.g., 4-6 mm, e.g., 5 mm.

In FIG. 1, impermeable barrier 140 is shown completely enveloping frame 50 to form a sealed bladder 40 having a wall 42 which is supported by expandable frame 50. Expandable frame 50 is reversibly expandable from a collapsed state to an expanded state, such that sealed bladder 40 assumes an expanded state completely encasing expandable frame 50 when expandable frame 50 is in the expanded state, as shown in FIG. 1.

It is additionally noted that contraceptive device 20 is deployed in Fallopian tube 104 in a reversible manner such that contraceptive device 20 can be removed from the tube lumen. To facilitate removal of contraceptive device 20 from the tube lumen, contraceptive device 20 further comprises a retrieval element 80, coupled, e.g., fixedly coupled, to frame 50 or barrier 140, (e.g., to sealed bladder 40). For example, retrieval element 80 comprises a cord or a thread, configured to facilitate removal of contraceptive device 20 from the lumen of tube 104 by dislodging of contraceptive device 20 from the lumen of tube 104 when the cord or thread 80 are pulled in a proximal direction.

It is noted that in this context, in the specification and in the claims, "proximal" means closer to the orifice through which the contraceptive device is originally placed into the body, and "distal" means farther from this orifice.

Reference is now made to FIGS. 2A-2G which are schematic illustrations of various configurations of contraceptive device 20, in accordance with some applications of the present invention.

Figure 2A:
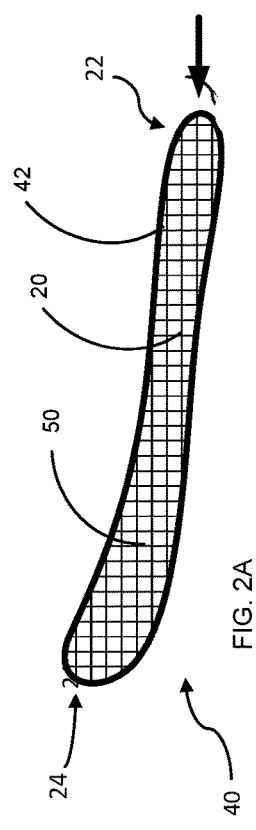
FIGS. 2A-B are schematic illustrations of configurations of the contraceptive device, in accordance with some applications of the present invention.
Figure 2B:
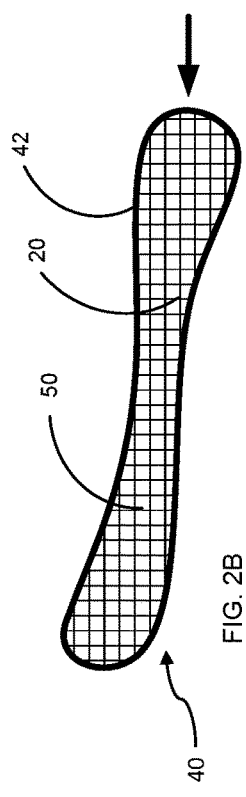

Reference is first made to FIGS. 2A-B which are schematic illustrations of contraceptive device 20, in accordance with some applications of the present invention.

Optionally but not necessarily, impermeable barrier 140 fully encases expandable frame 50 such that sealed bladder 40 is formed. Sealed bladder 40 has a bladder wall 42 which is supported by expandable frame 50. Expandable frame 50 is reversibly expandable from a collapsed state to an expanded state, such that sealed bladder 40 assumes an expanded state when expandable frame 50 is in the expanded state, as shown in FIGS. 2A-B.

For some applications, frame 50 is entirely integrated within or completely enveloped by bladder wall 42 such that bladder 40 is a sealed bladder. Typically, bladder wall 42 comprises a non-permeable bladder wall 42 preventing passage through bladder wall 42 and consequently through frame 50 and the tube lumen, when sealed bladder 40 is in the expanded state within the tube lumen and urged against the wall of the lumen. As described elsewhere herein, bladder wall 42 comprises a non-permeable elastic biocompatible material, e.g., polyurethane, silicone, EPTFE, and/or Dacron. It is noted that, the material comprising bladder 40 typically allows for an anatomically conformable pliable bladder 40, while inhibiting tissue in-growth into and onto contraceptive device 20 that may render the device non-retrievable.

Additionally, or alternatively, bladder wall 42 typically comprises a non-adhesive material inhibiting tissue in-growth in and on bladder 40, for ensuring the reversibility of contraceptive device 20 functionality and facilitating retrieval of contraceptive device 20 in simple and safe manner.

Typically, frame 50 comprises a shape memory material, e.g., nitinol, such that frame 50 self-expands upon deployment in the tube lumen. As shown in FIGS. 2A-B, for some applications, frame 50 comprises an expandable braided mesh. It is noted that frame 50 may be shaped to define alternative expandable structures such as struts or ribs. Expandable frame 50 supports bladder wall 42 such that when expandable frame 50 is in the expanded state, bladder 40 is expanded into a balloon-like configuration.

FIG. 2A shows expandable frame 50 shaped to define a tapered proximal portion 22 such that contraceptive device 20 assumes a tapered configuration to facilitate retrieval of contraceptive device 20 from tube 104.

Figure 2C:
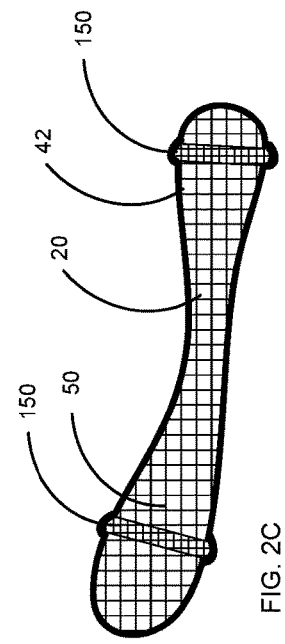
FIGS. 2C-D are schematic illustrations of the contraceptive device comprising circumferential anchoring portions, in accordance with some applications of the present invention.
Figure 2D:
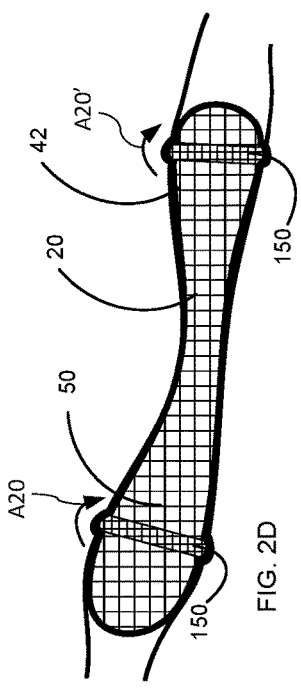

Reference is now made to FIGS. 2C-D which are schematic illustrations of contraceptive device 20 comprising a frame 50 having circumferential anchoring portions 150, in accordance with some applications of the present invention. In the exemplary application depicted in FIGS. 2C-D, impermeable barrier 140 is shown as fully encasing frame 50 to form sealed bladder 40. It is noted that, circumferential anchoring portions 150 may be used with other configurations of expandable frame 50 and impermeable barrier 140.

For some applications, expandable frame 50 comprises at least one circumferential portion 150 having a rigidity that is greater than a rigidity of remaining portions of the expandable frame 50. For some applications, circumferential portion 150 is formed in the expandable frame by, for example, providing additional layering and thickening of the mesh in circumferential portion 150 to create increased density in the circumferential portion 150 that is anchored against the wall of the tube lumen when contraceptive device 20 is disposed in the tube lumen. FIGS. 2C-D show expandable frame 50 having two circumferential portion 150 by way of illustration and not limitation. It is noted that expandable frame 50 may comprise any suitable number of circumferential portions 150.

Typically, when contraceptive device 20 is expanded in the tube lumen, circumferential portions 150 typically anchor contraceptive device 20 in the tube by applying pressure to the wall of tube in order to stabilize device 20 and reduce migration of contraceptive device 20 within the tube lumen. For some applications, the pressure applied by circumferential portions 150 is about 50% greater than the pressure applied by remaining portions of the expandable frame 50. Typically, circumferential portion 150 has a diameter of 2-15 mm.

Circumferential portions 150 typically increase stability of contraceptive device 20 in the tube lumen such that contraceptive device 20 remains generally stationary while forces are applied to contraceptive device 20 due to natural movements of the body tube (e.g., due to a peristaltic wave as indicated by arrows A20 and A20'). As noted, circumferential portions 150 typically function to anchor contraceptive device 20 in place in the tube and reduce migration of contraceptive device 20 in the tube, despite peristaltic waves to which tube 104 is subjected.

It is noted that circumferential portion 150 additionally provide an enhanced peripheral seal between impermeable barrier 140 (e.g., between wall 42) and the wall of the lumen of tube 104.

Figure 2F:
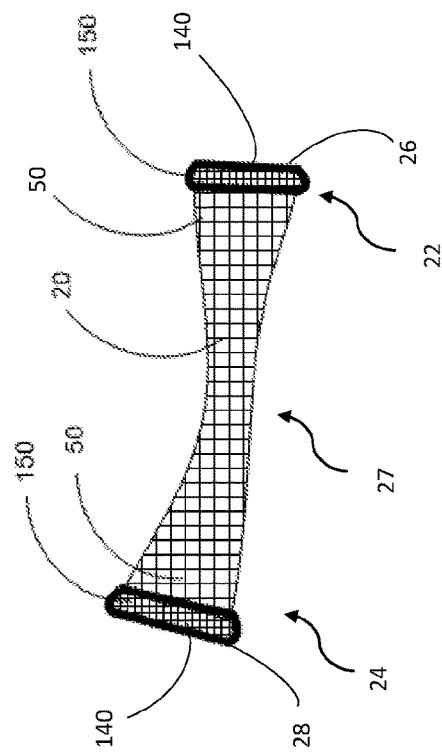
FIGS. 2E-F are schematic illustrations of additional configurations of the contraceptive device, in accordance with some applications of the present invention.
Figure 2E:
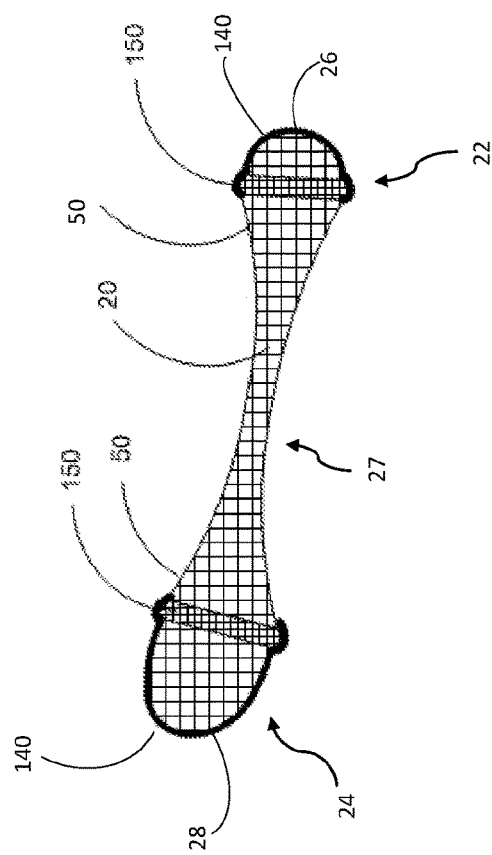

Reference is now made to FIGS. 2E-F, which are schematic illustrations of additional configurations of contraceptive device 20, in accordance with some applications of the present invention.

For some applications, in the expanded state, expandable frame 50 is expanded to define a peanut shape as shown in FIGS. 2E-F. Typically, expandable frame 50 has proximal portion 22, distal portion 24 and a middle portion 27 disposed between proximal and distal portions 22 and 24. As shown in FIGS. 2E-F, in some applications, when in the expanded state, a cross section of each one of proximal 22 and distal portion 24 is greater than a cross section of middle portion 27. For such applications, when expanded in a tube lumen, proximal and distal portions 22 and 24 of expandable frame 50 are urged against the walls of the lumen, whereas, middle portion 27 does not come in contact with the walls of the lumen (such that a gap is formed between middle portion 27 and walls of the tube lumen). Maintaining middle portion 27 at a distance from the walls of the tube lumen typically reduces the occurrence of tissue in-growth in and on contraceptive device 20, further ensuring safe and simple retrieval of contraceptive device 20.

For some applications, proximal portion 22 and distal portion 24 each have a cross section area that at a widest point thereof is 10-400% times greater than a cross section of middle portion 27. For some applications, a diameter of each one of proximal portion 22 and distal portion 24 is 20-100% greater than a diameter of middle portion 27.

Reference is still made to FIGS. 2E-F. for some applications, only proximal and distal portion 22 and 24 of expandable frame 50 support barrier 140, such that barrier 140 seals proximal and distal portions of expandable frame 50. For such applications, when expandable frame 50 is in an expanded state in the tube lumen, impermeable barrier 140 forms a double barrier by defining first and second tube lumen sealing surfaces 26 and 28. First and second sealing surfaces 26 and 28 are each disposed at an angle (e.g., generally perpendicular) with respect to the longitudinal axis of the tube and contact walls of lumen of tube 104 to form a double barrier by inhibiting passage proximally through first sealing surface 26 and distally through second surface 28. Typically, frame 50 is disposed between sealing surfaces 26 and 28 of barrier 140. Consequently, passage through expandable frame 50 and through the lumen of the tube in which expandable frame is expanded is blocked.

It is noted with reference to the configurations of contraceptive device 20 shown in FIGS. 2E-F, that barrier 140 may fully encapsulate all portions of frame 50.

Figure 2G:
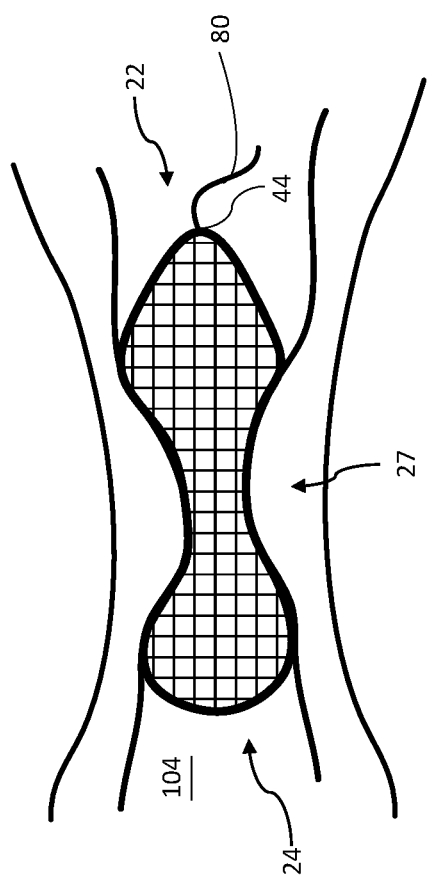
FIG. 2G is a schematic illustration of a peanut configuration of the contraceptive device, in accordance with some applications of the present invention.

Reference is now made to FIG. 2G. which is a schematic illustration of a peanut configuration of contraceptive device 20, in accordance with some applications of the present invention. As shown, and also as described elsewhere herein, contraceptive device 20 is typically shaped to resemble the shape of a peanut having by having proximal and distal portions 22 and 24 that are larger in diameter than middle portion 27. As described elsewhere herein, proximal and distal portions 22 and 24 may have a diameter that is 10-400%, e.g., 20-100% greater than a diameter of middle portion 27.

For some applications, the peanut shape facilitates deploying contraceptive device 20 in a uterotubal junction of Fallopian tube 104 by contraceptive device 20 conforming (at least in part) to the anatomical structure of the uterotubal junction of Fallopian tube 104. Additionally, or alternatively, as shown in FIG. 2G, contraceptive device 20 is shaped to define a conical proximal tip 44 for facilitating retrieval of contraceptive device 20 from Fallopian tube 104. Tip 44 is typically easily engageable by a grasper or crimping tool (not shown) thereby allowing grasping of contraceptive device 20 for easy and safe removal. It is noted that all configuration of contraceptive device 20 as shown herein may be shaped to define a conical tip 44. Reference is now made to FIGS. 3A-D which are schematic illustrations of contraceptive device 20 being advanced (FIG. 3A), deployed (FIG. 3B), maintained (FIG. 3C) and removed from tube 104 (FIG. 3D), in accordance with some applications of the present invention. By way of illustration and not limitation, in FIGS. 3A-D, contraceptive device 20 is shown such that barrier 140 completely encases frame 50, and frame 50 is radially expanded such that contraceptive device 20 assumes the configuration of sealed bladder 40 having wall 42 which is urged against walls of the lumen of tube 104. It is noted that any other expanded configuration of contraceptive device 20 (e.g., as shown in FIGS. 2E-F), may be disposed in tube 104, in accordance with some applications of the present invention.

Figure 3A:
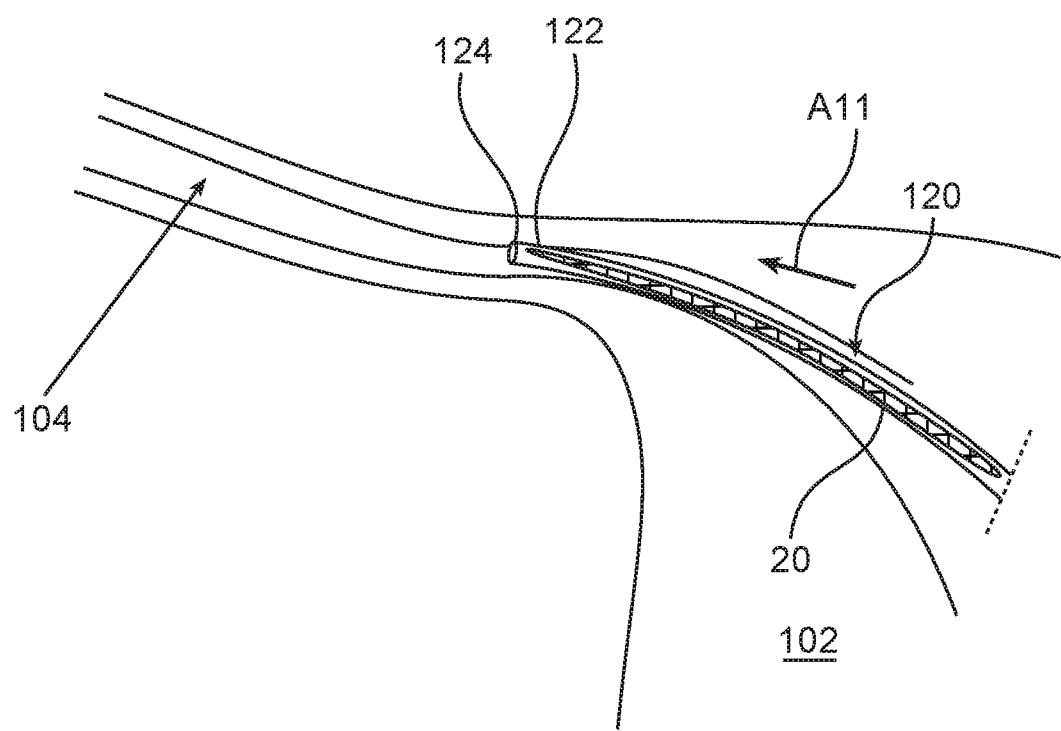
FIG. 3A is a schematic illustration of the contraceptive device being advanced into a lumen of a Fallopian tube of a subject in a collapsed state, in accordance with some applications of the present invention.

Reference is first made to FIG. 3A which is a schematic illustration of contraceptive device 20 being advanced into the lumen of Fallopian tube 104 of a subject in a collapsed state, in accordance with some applications of the present invention.

For some applications, contraceptive device 20 is deployed in a Fallopian tube 104 of a female subject in order to occlude the Fallopian tube in a manner that inhibits passage of reproductive cells through the lumen of the Fallopian tube 104 such that fertilization of the egg by the sperm is prevented. Typically, contraceptive device 20 is a long acting yet reversible contraceptive. Contraceptive device 20 is configured to remain in the Fallopian tube over time, and yet to be easily and safely removed from the Fallopian tube to restore the ability to conceive.

For some applications, a deployment tool 120 for advancing and deploying contraceptive device 20 in the lumen of tube 104, is provided. Typically, contraceptive device 20 is shaped and sized to be advanced in deployment tool 120 in the collapsed state and to self-expand upon release from deployment tool 120 in the tube lumen. For some applications, deployment tool 120 comprises sheath 122, (which is typically part of a delivery catheter), shaped and sized to surround contraceptive device 20 in the collapsed state thereof, and to advance contraceptive device 20 to a desired target in tube 104 in the body of the subject. Sheath 122 is additionally shaped to define a distally-facing port 124 for deploying contraceptive device 20 therethrough. Typically, contraceptive device 20 assumes the expanded state upon existing sheath 122.

Contraceptive device 20 is typically advanced transcervically through uterus 102 to the desired location in Fallopian tube 104 as indicated by arrow A11. As shown, contraceptive device 20 is advanced in a collapsed state within sheath 122 which is inserted through the cervix into uterus 102 and into Fallopian tube 104. For some applications, contraceptive device 20 is delivered to the desired location in fallopian tube 104 under visual or fluoroscopic guidance using markers (e.g., optical and/or radiopaque markers) on contraceptive device 20 and/or on sheath 122.

For some applications, prior to deployment of contraceptive device 20, data is collected regarding the anatomy of Fallopian tube 104 (e.g., a diameter and/or shape of the tube) in each individual subject, to assess an optimal deployment location for contraceptive device 20, and to select an optimally shaped and sized device 20 for each user. Additionally, or alternatively, device 20 can be shaped and sized to be compatible with a healthy Fallopian tube 104 or a Fallopian tube with a pathology. Further additionally, or alternatively, nanometric measurement for Fallopian tube 104 resistance at various locations along the tube, are conducted prior to deployment of contraceptive device 20 in order to further determine the optimal deployment location.

Figure 3B:
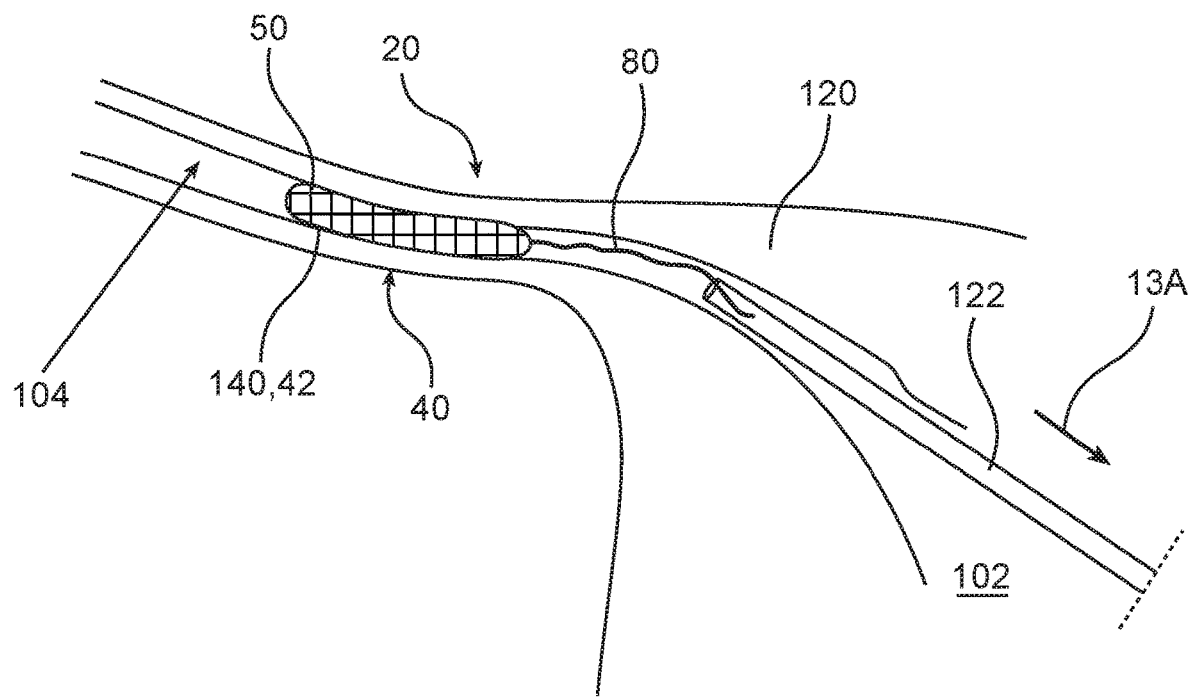
FIG. 3B is a schematic illustration of the contraceptive device being deployed in the lumen of the Fallopian tube to assume an expanded state, in accordance with some applications of the present invention.

Reference is now made to FIG. 3B which is a schematic illustration of the occlusion device being deployed in the lumen of the Fallopian tube to assume an expanded state, in accordance with some applications of the present invention. When sheath 122 arrives at the desired location in Fallopian tube 104, contraceptive device 20 is released from sheath 122, by withdrawing sheath 122 proximally in the direction indicated by arrow A13. Alternatively, contraceptive device 20 is released from sheath 122 by advancing device 20 distally out of sheath 122.

For some applications, contraceptive device 20 is deployed in the uterotubal junction which is the connection between the endometrial cavity of uterus 102 and Fallopian tube 104 at the proximal tubal opening of Fallopian tube 104. It is noted, however, that contraceptive device 20 may be deployed in any other suitable location along the lumen of Fallopian tube 104.

Typically, contraceptive device 20 is positioned in Fallopian tube 104 by a physician in an in-office procedure and does not require invasive measures or hospitalization.

Figure 3C:
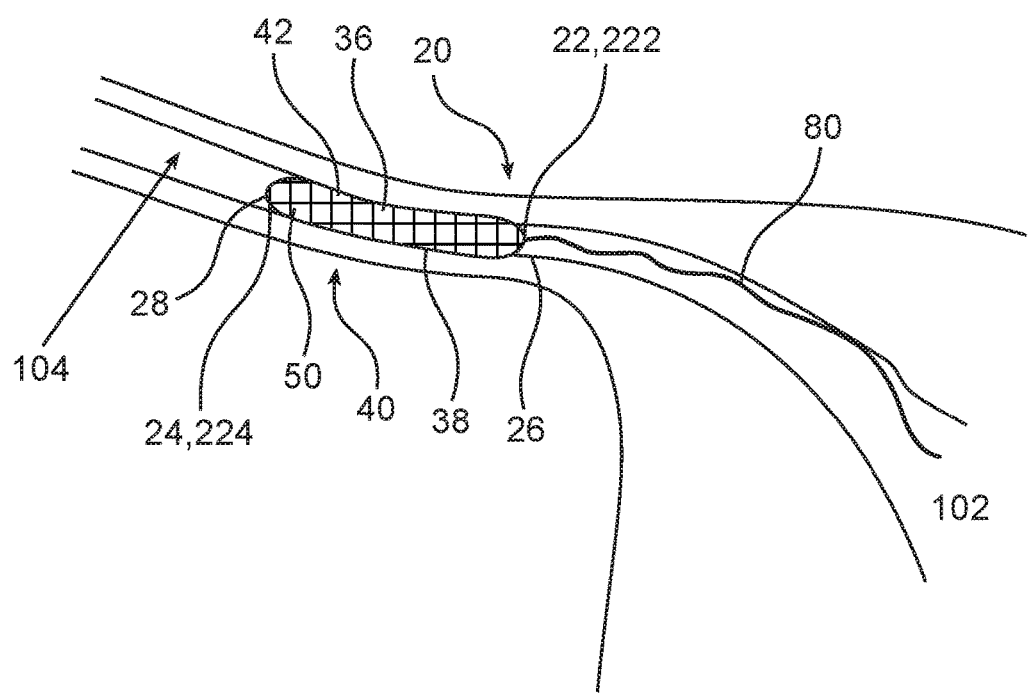
FIG. 3C is a schematic illustration of the contraceptive device deployed in the lumen of the Fallopian tube, in accordance with some applications of the present invention.

Reference is now made to FIG. 3C which is a schematic illustration of contraceptive device 20 deployed and maintained in the lumen of the Fallopian tube 104 in the expanded state, in accordance with some applications of the present invention. Upon release from sheath 122 (shown in FIG. 3B), contraceptive device 20 self-expands radially from the collapsed state into the expanded state shown in FIG. 3C. In the expanded state, frame 50 is expanded such that impermeable barrier 140 (shown as sealed bladder 40 having wall 42) which is supported by expandable frame 50 is expanded into an expanded state to occlude the lumen of Fallopian tube 104. Typically, bladder 40 expands in Fallopian tube 104 in a manner that conforms with the anatomy of the Fallopian tube achieving an enhanced seal and reducing migration of contraceptive device 20 in the Fallopian tube.

As shown, contraceptive device 20 is disposed in the lumen of Fallopian tube 104 such that when expanded in the lumen, wall 42 of the sealed bladder is urged against inner walls of Fallopian tube 104 resulting in occlusion of the Fallopian tube lumen.

When expanded inside the lumen of Fallopian tube 104, and against the walls of the tube lumen, wall 42 of sealed bladder 40 inhibits passage through the lumen by mechanically blocking the lumen. Wall 42 is a non-permeable wall such that passage, e.g., of reproductive cells, in an area blocked by sealed bladder 40 is prevented. In addition, since expandable frame 50 is completely encased by wall 42, passage through openings in the expandable frame 50 is prevented by wall 42. Thereby, in-growth of tissue in and on expandable frame 50 is prevented by wall 42. As shown, wall 42 of barrier 140 is disposed between frame 50 and the against inner walls of Fallopian tube 104 to inhibit tissue in-growth in and on contraceptive device 20. As described elsewhere herein, barrier 140 comprises an impermeable membrane having a non-adhesive coating, that prevents cells from penetrating the barrier and from attaching thereto.

Further additionally, wall 42 of sealed bladder 40 engages the walls of the lumen of Fallopian tube 104 to provide a complete seal between the wall of Fallopian tube lumen and sealed bladder 40 thereby providing a complete occlusion of the lumen of Fallopian tube 104.

For some applications, in the expanded state, wall 42 of sealed bladder 40 defines at least two wall-engaging surfaces 36 and 38 configured to be positioned against the inner walls along the longitudinal axis of Fallopian tube 104 to provide a complete seal between the wall of Fallopian tube lumen and sealed bladder 40.

Additionally, when expanded, wall 42 of sealed bladder 40 defines first and second tube lumen sealing surfaces 26 and 28 generally disposed at an angle (e.g., generally perpendicular) with respect to the longitudinal axis of Fallopian tube 104. Sealing surfaces 26 and 28 typically form a double barrier blocking passage of reproductive cells in Fallopian tube 104. In other words, sperm traveling distally in the Fallopian tube is typically inhibited from passage through the tube by sealing surface 26, and egg cells traveling proximally in the Fallopian tube are typically inhibited from passage through the tube by sealing surface 28. Thus, complete occlusion of Fallopian tube 104 is achieved.

Typically, first sealing surface 26 is supported by proximal end portion 222 at proximal portion 22 of expandable frame 50 and second sealing surface 28 is supported by distal end portion 224 at distal portion 24 of expandable frame 50, such that passage of reproductive cells is additionally blocked into and through expandable frame 50.

As shown, bladder 40 is completely disposed in the lumen of Fallopian tube 104 and does not penetrate tissue of the Fallopian tube. In addition, bladder 40 comprises a non-adhesive material inhibiting tissue in-growth.

Reference is still made to FIG. 3C. As shown, retrieval element 80 typically trails into uterus 102 when contraceptive device 20 is positioned in Fallopian tube 104, making retrieval element 80 accessible to a physician for cases in which it is desirable to remove contraceptive device 20 from Fallopian tube 104.

Figure 3D:
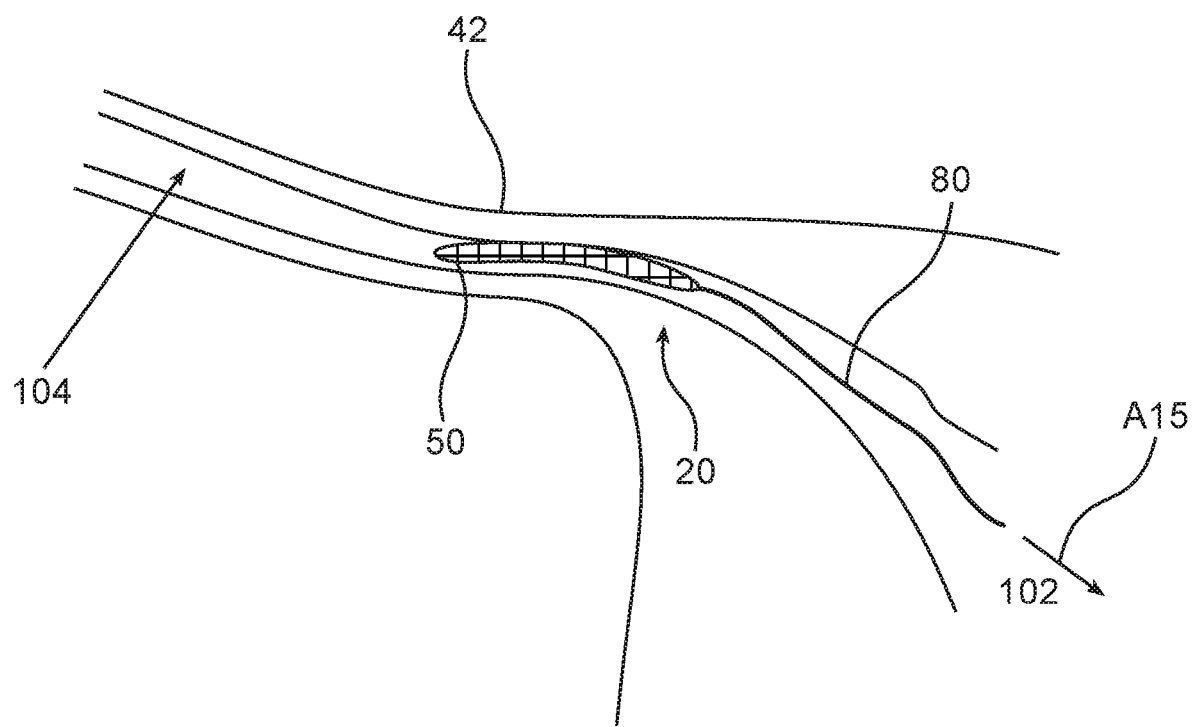
FIG. 3D is a schematic illustration of the contraceptive device being retrieved from the lumen of the Fallopian tube using a retrieval element, in accordance with some applications of the present invention.

Reference is now made to FIG. 3D which is a schematic illustration of contraceptive device 20 being retrieved from the lumen of the Fallopian tube using retrieval element 80, in accordance with some applications of the present invention. Typically, pulling of retrieval element 80 in the proximal direction indicated by arrow A15 causes slight narrowing of frame 50 such that contraceptive device 20 easily slides out of Fallopian tube 104.

It is noted that retrieval element 80 is shown as an elongated cord by way of illustration and not limitation. Retrieval element 80 may be shaped to define a loop coupled to bladder 40 and retrieval of bladder 40 is done using a hook to pull on the loop to retrieve bladder 40. Additionally, or alternatively, frame 50 may be shaped to define a retrieval element, e.g., a wire loop. For such applications, the wire loop may be encased by barrier 140 and a hook is used to tear barrier 140 and pull on the wire loop to retrieve contraceptive device 20.

Reference is now made to FIG. 3G which is a schematic illustration of contraceptive device 20 being retrieved from lumen of the Fallopian tube 104 using retrieval element 80, in accordance with another application of the present invention. As shown, for such applications, retrieval element 80 is coupled to a distal end of frame 50 (or barrier 140), such that pulling retrieval element 80 in the proximal direction causes folding and rolling of contraceptive device 20 away from the walls of tube 104 in a direction indicated by arrow A17, until contraceptive device 20 is completely removed from Fallopian tube 104.

Figure 3E:
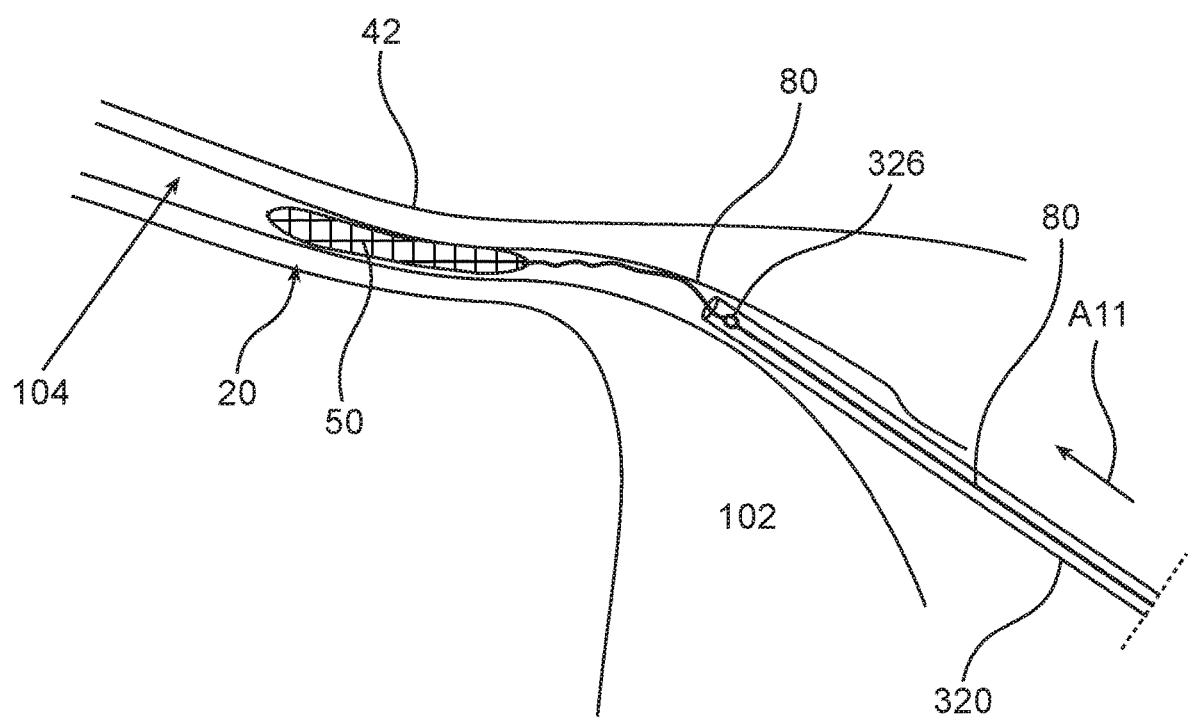
FIGS. 3E-F are schematic illustrations of the contraceptive device being retrieved from the lumen of the Fallopian tube additionally using a removal tool, in accordance with some applications of the present invention.
Figure 3F:
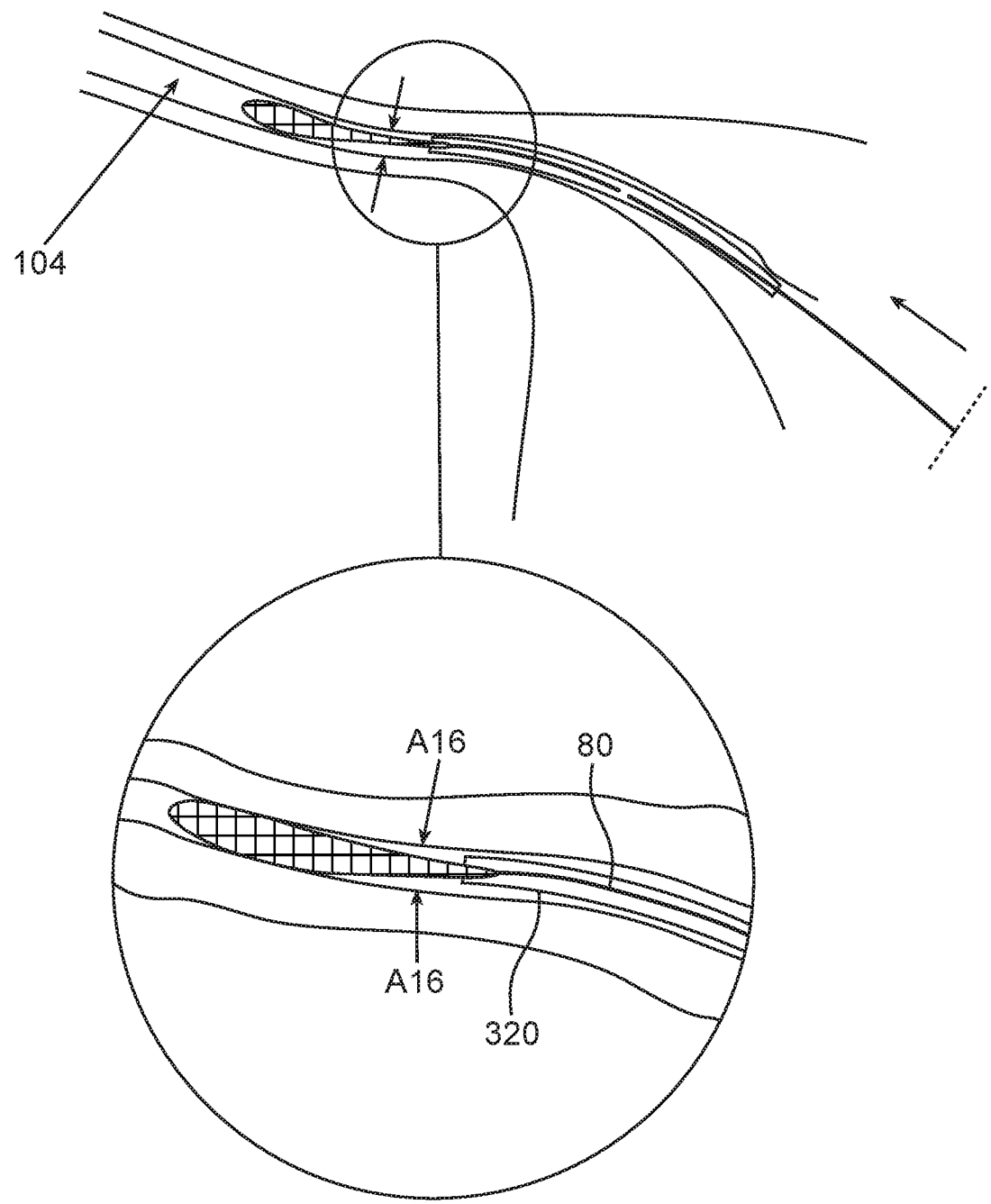

Reference is now made to FIGS. 3E-F which are schematic illustrations of contraceptive device 20 being retrieved from the lumen of Fallopian tube 104 additionally using a removal tool 320, in accordance with some applications of the present invention. For some applications, contraceptive device 20 is removed by additionally using removal tool 320. For example, removal tool 320 comprises an over-tube 320 which is shaped and sized to be advanced distally in the direction of arrow A11, and over contraceptive device 20 while causing radial compression, e.g., crimping, of contraceptive device 20 (indicated by arrows A16). Contraceptive device 20 is thereby engulfed by over-tube 320 and removed from Fallopian tube 104. For some applications, during distal advancement of over-tube 320 over contraceptive device 20, retrieval element 80 is used to stabilized device 20 and prevent distal movement contraceptive device 20 by anchoring to portion 326 of over-tube 320, as shown.

Reference is again made to FIGS. 3D and 3E-F. For some applications, following an attempt to retrieve contraceptive device 20 using only retrieval element 80 (e.g., pulling retrieval element 80 proximally), and encountering even a slight resistance, removal tool 320 is then introduced to ensure safe remove of contraceptive device 20.

It is noted that contraceptive device 20 can be permanently or temporarily removed (e.g., for relocation purposes) at any time following deployment of contraceptive device 20.

For some applications, subsequently to deploying contraceptive device 20 in lumen of Fallopian tube 104, it is desirable to unblock the tube and restore fertility. As described elsewhere herein, contraceptive device 20 may be entirely removed from tube 104, as shown in FIG. 3D. Alternatively, fertility is restored while contraceptive device 20 remains in the lumen of Fallopian tube 104. Typically, for such applications, barrier 140 is disrupted, e.g., punctured or torn, in a controlled manner by a physician, thereby allowing passage of reproductive cells through the frame and through the lumen of the Fallopian tube to restore fertility. It is noted that mechanical breach of barrier 140 does not occur spontaneously but rather in a controlled medical (typically in office) procedure. It is noted that any other mechanical mechanism of locally removing barrier 140 at the proximal and distal portions of contraceptive device 20, may be used to restore fertility.

In some cases, when it is desirable to re-occlude the Fallopian tube, an occluding element such as a balloon is inflated in the expandable frame to re-block the Fallopian tube to once again achieve the contraceptive functionality of contraceptive device 20. In another application, re-occlusion is achieved by replacing the breached device with a new contraceptive device 20.

For some applications a contraceptive kit is provided in accordance with some applications of the present invention. The kit typically comprises, contraceptive device 20, deployment tool 120, and removal tool 320.

Reference is now made to FIGS. 4A-B. As shown, FIG. 4A is a schematic illustration of a naturally occurring occlusion in 530 in Fallopian tube 104 causing infertility in a female, and FIG. 4B is a schematic illustration of a device 600 for treating infertility due naturally occurring occlusion 530 in Fallopian tube 104 causing infertility in a female, in accordance with some applications of the present invention.

In accordance with some applications of the present invention, an infertility treatment device 600 is provided for maintaining Fallopian tube 104 in an open configuration to treat occlusions (e.g., occlusion 530) in the tube that are typically due to a pathology. Typically, occlusions or adhesions in the Fallopian tube are known causes of infertility in women. In accordance with some applications of the present invention, a frame (similar to frame 50) is deployed and expanded in the Fallopian tube lumen to maintain the tube in an open configuration facilitating passage of reproductive cells through the tube to allow fertilization.

For some such applications a barrier (such as wall 42) may be coupled to the expandable frame such that when the frame is expanded in the Fallopian tube, the barrier is deployed against the inner walls along the longitudinal axis of the Fallopian tube. Typically, the barrier inhibits tissue in-growth on and in the frame that may render the device non-retrievable. For some applications the barrier is positioned on both inner and outer surfaces of frame 50 to line frame 50 and prevent an ectopic pregnancy by preventing a fertilized egg from getting caught in the frame. However, it is noted that passage through proximal and distal end portions of the frame are not interrupted by any barrier, thus allowing passage of reproductive cells through device 600 and Fallopian tube 104.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A contraceptive device comprising:
   an occluding component shaped and sized to be deployed in a tubal lumen of a reproductive organ and comprising:
   an expandable frame reversibly expandable from a collapsed state to an expanded state;
   a barrier comprising an impermeable membrane for both human sperm and oocyte, and supported by the expandable frame, such that when the frame is in the expanded state:
   a) the barrier is being peripheral and/or circumferential to the expandable frame;
   b) the barrier is characterized by a contour having at least one portion intended for contacting the internal walls of the tubal lumen to anchor the occluding component in the tubal lumen and to define a sealing surface such that passage of reproductive cells through the expandable frame, and through the tube-tubal lumen, is blocked when the expandable frame is expanded in the tube lumen.

2. The device according to claim 1, wherein the frame is encapsulated by the barrier.

3. The device according to claim 1, wherein the barrier has an inner surface and an outer surface and wherein the inner surface of the barrier is disposed on an outer surface of the expandable frame.

4. The device according to claim 1, wherein the expandable frame comprises an expandable shape-memory material; and wherein the barrier is further configured to be mechanically breached to allow passage of reproductive cells through the expandable frame, and through the tube lumen, when the expandable frame is expanded in the tube.

5. The device according to claim 1,
   wherein the expandable frame is shaped to define a proximal end portion at a proximal portion of the expandable frame and a distal end portion at a distal portion of the expandable frame, and
   wherein the barrier is urged against walls of the tubal lumen to define at least two tubal lumen sealing surfaces, and a first one of the at least two tube lumen sealing surfaces is supported by the proximal end portion such that passage through the proximal end portion of the expandable frame is blocked by the first sealing surface, and a second one of the two sealing surfaces is supported by the distal end portion such that passage through the distal end portion of the expandable frame is blocked by the second sealing surface.

6. The device according to claim 1, wherein the expandable frame comprises at least one circumferential portion having a rigidity that is greater than a rigidity of remaining portions of the expandable frame.

7. The device according to claim 1, comprising at least two circumferential portions, configured to contact the walls of the tube lumen to anchor the occluding component in the tube when the frame is in the expanded state.

8. The device according to claim 1, wherein the expandable frame has a proximal portion, a distal portion and a middle portion disposed between the proximal and distal portions and wherein when the frame is in the expanded state a cross section of each one of the proximal and distal portions is greater than a cross section of the middle portion such that a gap is formed between the middle portion and walls of the tube when the expandable frame is expanded in the tubal lumen.

9. The device according to claim 1, wherein the tubal lumen includes a lumen of a Fallopian tube and wherein the barrier is configured to urge against the inner walls of the Fallopian tube in the expanded state.

10. The device according to claim 1, wherein the barrier is disposed between both walls of the tubal lumen to inhibit in-growth of cellular material into and onto the occluding component.

11. The device according to claim 1, wherein the barrier comprises a sealed layer having a wall supported by the expandable frame such that when the expandable frame is in the expanded state the sealed layer is expanded into a corresponding expended state.

12. A kit comprising:
   a contraceptive device comprising:
      (i) an occluding component of claim 1;
   a deployment tool configured to advance the contraceptive device into a tubal lumen; and
   a removal tool configured to remove the contraceptive device from the tube lumen.

13. A contraceptive device comprising:
   an occluding component shaped and sized to be deployed in a tubal lumen of a reproductive organ and comprising:
      an expandable frame having a proximal portion, a distal portion and a middle portion disposed between proximal and distal portions, and reversibly expandable from a collapsed state to an expanded state; and
      a barrier comprising an impermeable membrane for both human sperm and oocyte, and supported by the expandable frame, such that when the frame is in the expanded state:
         (a) the barrier is urged against walls of the tubal lumen to anchor the occluding component in the tubal lumen and to define at least two tube lumen sealing areas, each disposed perpendicular with respect to a longitudinal axis of the walls of the tubal lumen such that (i) the expandable frame is disposed between the two tube lumen sealing areas, and (ii) passage of reproductive cells through the expandable frame, and through the tubal lumen, is blocked; and
         (b) a cross section of each one of the proximal and distal portions is greater than a cross section of the middle portion such that a gap is formed between the middle portion and walls of the tube when the expandable frame is expanded in the tubal lumen.

14. A contraceptive device comprising:
   an occluding component shaped and sized to be deployed in a tubal lumen of a reproductive organ and comprising:
      an expandable frame having a proximal portion, a distal portion and a middle portion disposed between proximal and distal portions, and reversibly expandable from a collapsed state to an expanded state;

a barrier comprising an impermeable membrane for both human sperm and oocyte, and supported by the expandable frame, such that when the frame is in the expanded state:

a) the barrier is being peripheral and/or circumferential to the expandable frame;

b) the barrier is characterized by a contour having at least one portion intended for contacting the internal walls of the tubal lumen to anchor the occluding component in the tubal lumen and to anchor the occluding component in the tubal lumen and to define a sealing surface such that passage of reproductive cells through the expandable frame, and through the tubal lumen, is blocked when the expandable frame is expanded in the tube;

wherein a cross section of each one of the proximal and distal portions is greater than a cross section of the middle portion such that a gap is formed between the middle portion and walls of the tube when the expandable frame is expanded in the tubal lumen.

* * * * *